US008167946B2

(12) United States Patent
Michelson

(10) Patent No.: US 8,167,946 B2
(45) Date of Patent: *May 1, 2012

(54) IMPLANT WITH OPENINGS ADAPTED TO RECEIVE BONE SCREWS

(75) Inventor: Gary K. Michelson, Venice, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/807,784

(22) Filed: Sep. 14, 2010

(65) Prior Publication Data

US 2011/0009966 A1  Jan. 13, 2011

Related U.S. Application Data

(63) Continuation of application No. 12/290,180, filed on Oct. 28, 2008, now Pat. No. 7,794,502, which is a continuation of application No. 11/291,038, filed on Nov. 30, 2005, now Pat. No. 7,442,209, which is a continuation of application No. 09/768,991, filed on Jan. 23, 2001, now Pat. No. 6,972,019.

(51) Int. Cl.
*A61F 2/44* (2006.01)
(52) U.S. Cl. .................................. 623/17.11
(58) Field of Classification Search .... 623/17.11–17.16; 606/301
See application file for complete search history.

(56) References Cited

U.S. PATENT DOCUMENTS

| 2,065,659 A | 8/1934 | Cullen |
| 2,181,746 A | 11/1939 | Siebrandt |
| 2,774,350 A | 12/1956 | Cleveland, Jr. |
| 3,298,372 A | 1/1967 | Feinberg |
| 3,426,364 A | 2/1969 | Lumb |
| 3,875,595 A | 4/1975 | Froning |
| 3,916,907 A | 11/1975 | Peterson |
| 4,047,524 A | 9/1977 | Hall |
| 4,059,115 A | 11/1977 | Jumashev et al. |
| 4,271,832 A | 6/1981 | Evans et al. |

(Continued)

FOREIGN PATENT DOCUMENTS

DE  3 132 520  6/1982

(Continued)

OTHER PUBLICATIONS

European Search Report dated Jul. 27, 1998 from European Application No. EP 95 91 4197.

(Continued)

*Primary Examiner* — Pedro Philogene
(74) *Attorney, Agent, or Firm* — Martin & Ferraro, LLP

(57) ABSTRACT

A spinal fusion implant for insertion between adjacent vertebral bodies has opposed upper and lower surfaces adapted to contact each of the adjacent vertebral bodies from within the disc space, a leading end for insertion between the adjacent vertebral bodies, and a trailing end opposite the leading end. The trailing end has an exterior surface and an outer perimeter with an upper edge and a lower edge adapted to be oriented toward the adjacent vertebral bodies, respectively, and a plurality of bone screw receiving holes. At least one of the bone screw receiving holes is adapted to only partially circumferentially surround a trailing end of a bone screw received therein. At least one of the bone screw receiving holes passes through the exterior surface and one of the edges so as to permit the trailing end of the bone screw to protrude beyond one of the edges.

20 Claims, 6 Drawing Sheets

U.S. PATENT DOCUMENTS

| | | | | |
|---|---|---|---|---|
| 4,289,123 | A | 9/1981 | Dunn | |
| 4,294,753 | A | 10/1981 | Urist | |
| 4,401,112 | A | 8/1983 | Rezaian | |
| 4,439,152 | A | 3/1984 | Small | |
| 4,455,256 | A | 6/1984 | Urist | |
| 4,526,909 | A | 7/1985 | Urist | |
| 4,554,914 | A | 11/1985 | Kapp et al. | |
| D281,814 | S | 12/1985 | Pratt et al. | |
| 4,563,489 | A | 1/1986 | Urist | |
| 4,570,623 | A | 2/1986 | Ellison et al. | |
| 4,570,624 | A | 2/1986 | Wu | |
| 4,592,346 | A | 6/1986 | Jurgutis | |
| 4,596,574 | A | 6/1986 | Urist | |
| 4,599,086 | A | 7/1986 | Doty | |
| 4,604,995 | A | 8/1986 | Stephens et al. | |
| 4,611,581 | A | 9/1986 | Steffee | |
| 350,420 | | 10/1986 | Dillon | |
| 4,619,989 | A | 10/1986 | Urist | |
| 4,696,290 | A | 9/1987 | Steffee | |
| 4,743,256 | A | 5/1988 | Brantigan | |
| 4,743,260 | A | 5/1988 | Burton | |
| 4,759,769 | A | 7/1988 | Hedman et al. | |
| 4,761,471 | A | 8/1988 | Urist | |
| 4,789,732 | A | 12/1988 | Urist | |
| 4,795,804 | A | 1/1989 | Urist | |
| 4,805,602 | A | 2/1989 | Puno et al. | |
| 4,857,456 | A | 8/1989 | Urist | |
| 4,877,020 | A | 10/1989 | Vich | |
| 4,878,915 | A | 11/1989 | Brantigan | |
| 4,903,882 | A | 2/1990 | Long | |
| 4,904,261 | A | 2/1990 | Dove et al. | |
| 4,913,144 | A | 4/1990 | Del Medico | |
| 4,955,908 | A | 9/1990 | Frey et al. | |
| 4,960,420 | A | 10/1990 | Goble et al. | |
| 5,015,247 | A | 5/1991 | Michelson | |
| 5,026,373 | A | 6/1991 | Ray et al. | |
| 5,084,048 | A | 1/1992 | Jacob et al. | |
| 5,092,893 | A | 3/1992 | Smith | |
| 5,108,422 | A | 4/1992 | Green et al. | |
| 5,258,031 | A | 11/1993 | Salib et al. | |
| 5,306,307 | A | 4/1994 | Senter et al. | |
| 5,314,427 | A | 5/1994 | Goble et al. | |
| 5,352,229 | A | 10/1994 | Goble et al. | |
| 5,364,399 | A * | 11/1994 | Lowery et al. | 606/295 |
| 5,395,372 | A | 3/1995 | Holt et al. | |
| 5,397,364 | A | 3/1995 | Kozak et al. | |
| 5,534,031 | A | 7/1996 | Matsuzaki et al. | |
| 5,556,431 | A | 9/1996 | Buttner-Janz | |
| 5,562,663 | A | 10/1996 | Wisnewski et al. | |
| 5,674,296 | A | 10/1997 | Bryan et al. | |
| 5,702,449 | A | 12/1997 | McKay | |
| 5,776,199 | A | 7/1998 | Michelson | |
| 5,800,433 | A * | 9/1998 | Benzel et al. | 606/250 |
| 6,066,175 | A | 5/2000 | Henderson et al. | |
| 6,099,531 | A | 8/2000 | Bonutti | |
| 6,129,763 | A * | 10/2000 | Chauvin et al. | 623/17.11 |
| 6,139,550 | A | 10/2000 | Michelson | |
| 6,143,032 | A | 11/2000 | Schafer et al. | |
| 6,159,214 | A | 12/2000 | Michelson | |
| 6,193,721 | B1 | 2/2001 | Michelson | |
| 6,214,005 | B1 | 4/2001 | Benzel et al. | |
| 6,224,607 | B1 | 5/2001 | Michelson | |
| 6,231,610 | B1 | 5/2001 | Geisler | |
| 6,235,059 | B1 | 5/2001 | Benezech et al. | |
| 6,342,074 | B1 | 1/2002 | Simpson | |
| 6,432,106 | B1 | 8/2002 | Fraser | |
| 6,558,423 | B1 | 5/2003 | Michelson | |
| 6,629,998 | B1 | 10/2003 | Lin | |
| 6,824,564 | B2 * | 11/2004 | Crozet | 623/17.11 |
| 6,972,019 | B2 * | 12/2005 | Michelson | 606/86 A |
| 7,442,209 | B2 * | 10/2008 | Michelson | 623/17.11 |
| 7,794,502 | B2 * | 9/2010 | Michelson | 623/17.16 |
| 2002/0161445 | A1 | 10/2002 | Crozet | |

FOREIGN PATENT DOCUMENTS

| | | |
|---|---|---|
| EP | 0 077 159 | 4/1983 |
| EP | 0 179 695 | 4/1986 |
| EP | 0 307 241 | 3/1989 |
| EP | 0 551 187 | 7/1993 |
| EP | 0 552 109 | 7/1993 |
| EP | 0 809 971 | 12/1997 |
| EP | 1 769 777 | 4/1998 |
| ES | 2 048 671 | 3/1994 |
| FR | 2 709 410 | 3/1995 |
| GB | 2 082 754 | 3/1982 |
| GB | 2 207 607 | 2/1989 |
| JP | 60-31706 | 2/1985 |
| SE | 106 101 | 10/1942 |
| SU | 1 107 854 | 8/1984 |
| WO | WO 98/48738 | 11/1998 |
| WO | WO 00/66045 | 11/2000 |

OTHER PUBLICATIONS

PCT International Search Report dated Jul. 3, 1995 from International Application No. PCT/US95/03770.

Rathke, F.W., et al.; Surgery of the Spine; Atlas of Orthopaedic Operations, vol. 1, p. 137, W.B. Saunders Co., Philadelphia (1979).

Morscher, E., et al.; Die vordere Verplattung der Halswirbelsaule mit dem Hohlschrauben-Plattensystem aus Titanium, *Der Chirurg*, vol. 57, pp. 702-707 (1986) with English Translation.

* cited by examiner

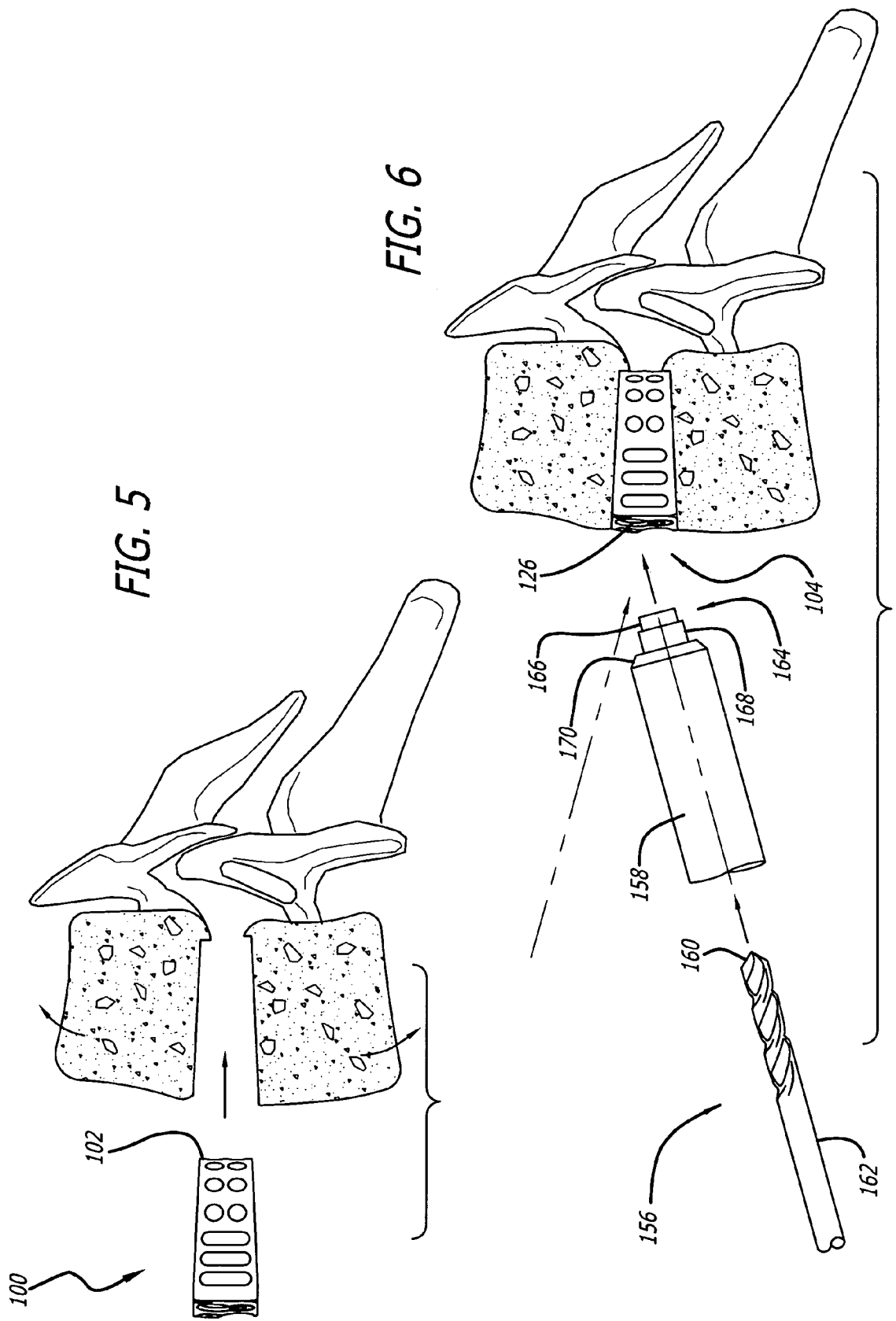

IMPLANT WITH OPENINGS ADAPTED TO RECEIVE BONE SCREWS

The present application is a continuation of application Ser. No. 12/290,180, filed on Oct. 28, 2008, now U.S. Pat. No. 7,794,502; which is a continuation of application Ser. No. 11/291,038, filed on Nov. 30, 2005, now U.S. Pat. No. 7,442,209; which is a continuation of application Ser. No. 09/768,991, filed on Jan. 23, 2001, now U.S. Pat. No. 6,972,019; all of which are incorporated herein by reference.

BACKGROUND OF THE INVENTION

Implants adapted for use in the lumbar spine and the thoracic spine become much less usable in the cervical spine because of differences in anatomy. In the lumbar spine, the disc spaces are about 25% as tall as the vertebral bodies (i.e., the vertebral bodies are generally four times taller than the intervening disc space). In the cervical spine, the disc space can be 50% of the height of the vertebral bodies. The disc spaces in the cervical spine are generally not greater than 7 or 8 mm tall in most people.

Screws generally used to secure an implant in the cervical spine typically have a diameter of between 4 and 5 mm. If two bone screws were to be inserted one each into each of the adjacent cervical vertebral bodies; and if one were to attempt to vertically oppose those two bone screws, this would not prove possible because the sum of the screw diameters would exceed the height of the implant. Such vertically aligned bone screws would require at least 10 mm of combined height for themselves plus sufficient implant structure and further height sufficient to surround and retain them. Thus, altogether the two bone screws and the surrounding implant would have to have a combined height that would substantially exceed the height of the disc space and an implant adapted to fit therein.

Alternatively, one could try to place a number of bone screws more horizontally (side-by-side) so as to avoid the problems described above associated with vertical alignment. To provide for the preferred implant stability that the use of paired screws would provide (two each into each of the adjacent vertebral bodies), one could horizontally align four bone screws on the equator of the implant with two of the bone screws directed toward one of the cervical vertebral bodies and two of the bone screws directed toward the other of the adjacent cervical vertebral bodies. Four such horizontally aligned bone screws having a head diameter of 5 mm each would require at least 20 mm for the screw heads alone. Further, with sufficient implant structure to surround each of those screw heads, the implant width would at a minimum be about 24 mm, which would exceed the desirable implant width for most cervical disc spaces. Staggering the bone screw receiving holes would be of some benefit, but of itself not an adequate solution to the problem described where it is desirable to maintain some symmetry of the screws to each other, the vertebrae, and the implant.

One prior art solution to the aforementioned problem teaches extending the height of the trailing end of the implant to make it taller than the disc space. An example of this is a flanged implant. The flanged implant makes it possible to place screws so that they can be vertically aligned and have sufficient structure of the implant to retain them. The flanged portion of the implant, however, extends outside of the disc space which may not be desirable in all circumstances. Further, these flanged implants may not be usable when it is needed to fuse multiple levels of the spine.

Accordingly, there exists a need for a spinal implant adapted to provide the advantages of a flanged implant for placement and orientation of bone screws associated therewith but without the flanged portion, or the necessity of the implant extending outside of the disc space.

SUMMARY OF THE INVENTION

The present invention is directed to an interbody spinal implant, such as but not limited to a spinal fusion implant, spacers, motion preserving implants, or others. The implant has opposed upper and lower surfaces, one each for contacting each of the opposed vertebral bodies adjacent a disc space. The implant is adapted to cooperatively receive at least two opposed bone screws, at least one screw each for insertion into each of the vertebral bodies adjacent a disc space. The interbody spinal implant is adapted to receive the bone screws through its trailing end and to allow for the passage of the leading end of the bone screws through at least a portion of the implant and out of the opposed upper or lower implant surfaces, one each respectively. The bone screws have a leading end, a shaft, threading upon the shaft, and a trailing end. The implant and the trailing end of the bone screw are adapted to cooperatively engage each other so as to prevent the further advance of the bone screws through the implant. At least a portion of the perimeter of the trailing ends of at least some of the bone screws protrude beyond at least one of the opposed upper or lower implant surfaces.

In one preferred embodiment, the trailing end is configured to permit a portion of the head of at least one bone screw to protrude beyond the height of the perimeter of the trailing end. The trailing end of the implant includes at least one bone screw receiving opening or hole that has a gap in the perimeter thereof for permitting at least a portion of the trailing end of a bone screw to protrude beyond the opposed upper or lower vertebral body engaging surfaces. The gap interrupts the perimeter of the bone screw receiving hole, so that the bone screw receiving hole has an incomplete perimeter or C-shape. The gap is sized such that it is less than half the diameter of the screw. By allowing the screws to each protrude over either the upper or lower edges of the implant trailing end, the upper and lower screws may be placed such that the maximum height of the implant trailing end is less than the sum of the maximum diameter of two bone screws adapted to be inserted in the bone screw receiving holes. This permits the use of larger bone screws in the trailing end of the implant than would otherwise be possible. Further, though not so limited, the present invention allows bone screws of the optimal diameter to be inserted into and in part through the implant and into the adjacent vertebral bodies without the necessity of a portion of the implant itself extending beyond the disc space and outside of the spine.

The trailing end of the implant is configured to permit the bone screws for insertion into each of the adjacent vertebrae to be angled relative to each other, the implant trailing end, and to the implant upper and lower surfaces. The opposed bone screws preferably pull the anterior aspects of the vertebral bodies together toward the implant. The bone screws preferably penetrate into a portion of the vertebral body closest to the disc space into which the implant is being installed so as not to interfere with bone screws from a second implant being installed in an adjacent disc space where consecutive levels of the spine are being fused. In a preferred embodiment, the trailing end is configured to lag the bone screws so as to compress the vertebral bodies together and to load the vertebral body implant interface to promote fusion.

In certain preferred embodiments, the screws subtend an angle with the upper and lower surfaces so as to keep them confined to the lower half of the vertebral body above or the upper half of the vertebral body below the disc space to be fused.

In other preferred embodiments, the trailing end of the implant is configured to allow screws that are originating at or close to the vertical midline of the trailing end of the implant to be directed outward, or divergently oriented; and screws that originate further from the vertical midline of the trailing end of the implant to be directed inward, or convergently oriented. The screws that are convergently oriented are directed to one vertebral body and the screws that are divergently oriented are directed to the other adjacent vertebral body. Such an arrangement permits such implants when inserted into adjoining disc spaces to have convergently oriented screws from one implant and divergently oriented screws from the other implant to be screwed into the same vertebral body and ensure that the screws do not interfere with one another. Such a configuration allows screws from different implants to pass each other within a vertebral body where both adjacent disc spaces are to be fused.

In any of these embodiments it is preferred though not required that the screws be retained to the implant by "locking mechanisms" which may include any of those known to those skilled in the art including, but not limited to, those taught by applicant, for example, U.S. Pat. No. 6,139,550, titled "Skeletal Plating System," U.S. application Ser. No. 09/022,293 titled "Anterior Cervical Plating System, Instrumentation, and Method of Installation," and U.S. application Ser. No. 09/565,392 titled "Interbody Spinal Fusion Implants with Opposed Locking Screws", all of which are incorporated herein by reference. The trailing end of the implant may be configured to receive bone screws such that they are constrained within the bone screw receiving holes (i.e., fixing the trajectory of each bone screw), or left unconstrained within the bone screw receiving holes for allowing variable screw angles. If a locking mechanism is used, the screws may start out constrained within the bone screw receiving holes and remain so when locked. Alternatively, the screws may start out unconstrained prior to locking them, and upon being locked, may be constrained by the screw lock or left unconstrained by the screw lock. Examples are described below.

If it is desired to have the bone screws constrained in the bone screw receiving holes then the bone screw receiving holes may be adapted to capture the screws. Preferably, an interference fit is formed between the wall of the bone screw receiving hole and the screw to prevent the screws from moving within the bone screw receiving hole.

The screws may also be self-locking with cooperative mating threads between the screw head and the bone screw receiving hole. An example of a preferred self-locking bone screw may be found in applicant's application Ser. No. 09/565,392 titled "Spinal Implant with Vertebral Endplate Engaging Anchor" incorporated herein by reference.

If it is desired that the bone screws are unconstrained then the bone screws may have a rounded head portion and/or a reduced neck diameter to permit movement of the bone screws so as to allow the angle between the implant and the bone screw to be variable.

If it is desired to lock the bone screw, the locking mechanism may be adapted to leave the bone screw constrained or unconstrained by adapting the interior surface of the locking mechanism accordingly. For example, the end of a screw lock facing a screw head may be concave to accommodate a round screw head, thereby allowing an unconstrained screw to be locked to the implant, yet still permit variable screw angles relative to the implant. Alternatively, the locking mechanism may be configured to constrain an unconstrained bone screw by having the lock forcefully bear upon the screw head.

Although bone screw locks are preferred, the invention is not so limited. Bone screws need not be locked to the implant, but simply may have, for example, a stop or shoulder for stopping the progress of a bone screw through the implant beyond a certain point along the bone screw length.

The bone screw heads are preferably but not necessarily flush or slightly below the exterior surface of the trailing end of the implant when fully installed so as not to substantially protrude therefrom as into delicate anatomical structures that may be present proximate the exterior surface of the trailing end of the implant.

The implant of the present invention is useful throughout the spine, including the cervical, thoracic, and lumbar portions, and depending upon the location, may be inserted from the anterior, posterior, or lateral aspects of the spine.

Many of the preferred embodiments of the present invention have one or more of the following advantages over the prior art. One advantage is a more shallow screw angle between the screw and the implant. A more shallow screw angle provides the screws with additional anchoring force. The ability of the screw to anchor in the bone is proportional to the amount of threaded surface area. As the screw gets longer, its bite gets better. Therefore, a more shallow screw angle permits the screw to stay in a short height body longer.

Another advantage is that by starting with the screw close to the implant surface and having the screw exit the implant sooner, less of the screw will be in the implant, thereby providing more space within the implant for fusion promoting substances or other desired contents.

A further advantage is the accommodation of the trailing ends of bone screws within the depth of the disc space to reduce the risk of damage to adjacent delicate structures, including but not limited to proximate vascular and neurological structures within the body. Parts of implants extending beyond the depth of the disc space may have a risk of damaging these adjacent delicate structures. It should be understood that the accommodation of the trailing ends of bone screws within the depth of the disc space is a preferred embodiment only and that the invention is not so limited.

A further advantage is the ability of the bone screws to exit the implant quicker and engage an adjacent vertebral body. A trailing end of a bone screw that is closer to the equator of the implant (i.e., the horizontal mid-line of the trailing end) and further from the opposed upper or lower surfaces of the implant takes longer for the threaded portion of the screw to leave the implant. In contrast, the present invention in one or more preferred embodiments allows the threaded portion of a bone screw to leave the implant sooner at a shallower angle and to thereby have additional threaded length than otherwise would be achieved if more of the threaded portion were within the trailing end of the implant.

While the above-described configurations are preferred for various advantages they do not in any way limit the breadth of the present invention, which is limited only by the claims.

BRIEF DESCRIPTION OF THE DRAWINGS

FIG. 5 is a side elevation view of an embodiment of the spinal implant of the present invention shown being inserted into an implantation space formed across the disc space between two adjacent vertebral bodies of the spine shown in partial cross-section.

FIG. 6 is a side elevation view of a drill and drill guide for forming bone screw receiving openings into adjacent vertebral bodies corresponding to bone screw receiving holes in the trailing end of the spinal implant of the present invention implanted between two adjacent vertebral bodies shown in partial cross-section.

DETAILED DESCRIPTION OF THE DRAWINGS

Figure 1:
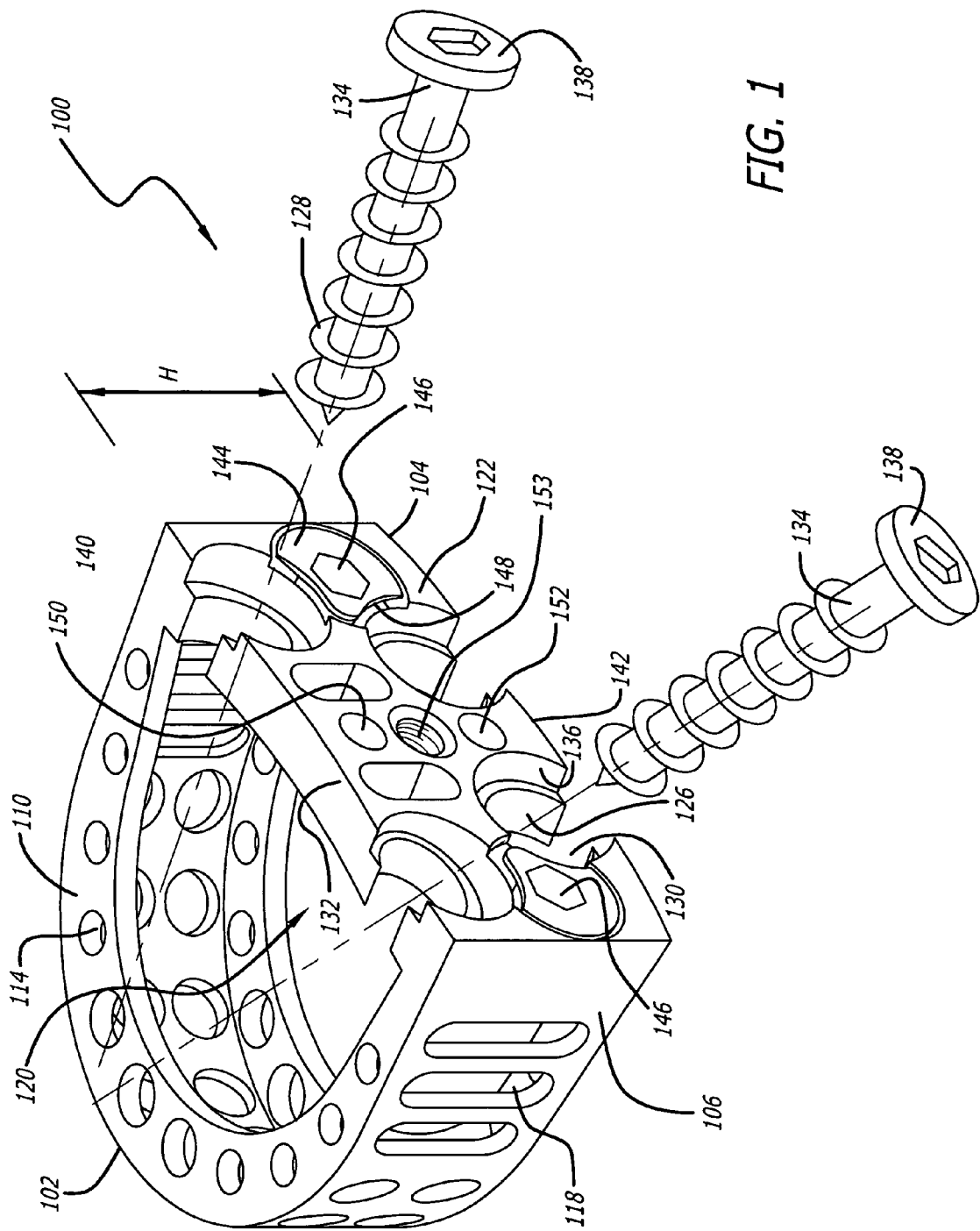
FIG. 1 is a trailing end perspective view of an embodiment of the spinal implant of the present invention.
Figure 2:
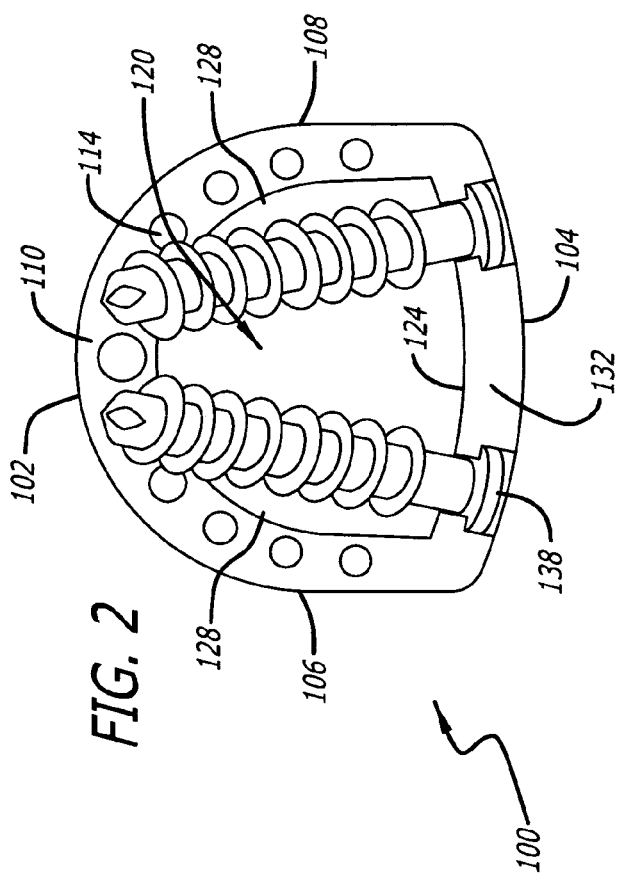
FIG. 2 is a top plan view of the spinal implant of FIG. 1.

Reference will now be made in detail to the present preferred embodiments of this invention, examples of which are illustrated in the accompanying drawings. Similar reference numbers such as "102, 202" will be used throughout the drawings to refer to similar portions of different embodiments of the present invention.

As shown in FIGS. 1-4, a preferred embodiment of the spinal implant of the present invention is generally referred to by the numeral 100. As used herein, the term "implant" includes any device adapted for insertion between two adjacent vertebral bodies, for example only, spacers, bone dowels, and spinal fusion implants. Implant 100 has a leading end 102, an opposite trailing end 104, and sides 106 and 108 therebetween for connecting, spanning, or joining, ends 102, 104.

In a preferred embodiment, leading end 102 can be a portion of a circle and the implant width can be equal to that portion of the circle, or if a half circle, then the diameter of that circle. Alternatively, leading end 102 may be straight at least in part, and for example the straight part can be at an approximately right angle to sides 106, 108 to form a generally rectangular or square shape. The configuration of the leading end of the implant of the present invention may be adapted to match the configuration of an implantation space formed across the disc space and into the adjacent vertebral bodies in accordance with U.S. Pat. No. 6,159,214 titled "Milling Instrumentation and Method for Preparing a Space Between Adjacent Vertebral Bodies" and applicant's co-pending patent application Ser. No. 09/490,901 titled "Instrument and Method for Creating an Intervertebral Space for Receiving an Implant," both of which are incorporated by reference herein.

Implant 100 has a vertebral body engaging upper surface 110 and an opposite vertebral body engaging lower surface 112. In a preferred embodiment, upper and lower surfaces 110, 112 may be convergent toward one another such that implant 100 is able to place the adjacent vertebral bodies in angular relationship to each other, for example, in lordosis. Upper and lower surfaces 110, 112 may have at least one opening 114 therethrough for permitting the growth of bone from adjacent vertebral body to adjacent vertebral body through implant 100.

Both ends 102 and 104 may include openings such as 116 so as to permit for the growth of bone and vascular access therethrough. Similarly, sides 106, 108 can include openings such as 118 for similar or other purposes. Implant 100 preferably has an open interior 120 between sides 106, 108 to permit for the growth of bone from adjacent vertebral body to adjacent vertebral body therethrough. The implant 100 itself, any of its various surfaces, open interior 120 and/or any of its openings such as 114, 116, 118, for example, can be coated with, or contain bone growth promoting materials, including but not limited to, bone, bone morphogenetic proteins, hydroxyapatite, genes coding for the production of bone, or any other material that intrinsically participates in the growth of bone from one of the adjacent vertebral bodies to the other of the adjacent vertebral bodies at the fusion site. Implant 100 may also be combined with a chemical substance to inhibit scar formation.

In a preferred embodiment, trailing end 104 has an exterior surface 122 and an interior surface 124. At least exterior surface 122 may be curved to conform to at least a portion of the natural curvature of the anterior aspect of the vertebral bodies. For example, exterior surface 122 may be concave in a horizontal plane, in a vertical plane, or biconcave in both the vertical and horizontal planes. Exterior surface 122 may, but need not, correspond to the configuration of interior surface 124. In the preferred embodiment, exterior surface 122 is configured to eliminate sharp edges and corners to protect the adjacent delicate vascular and neurological structures within the body. For example, exterior surface 122 can be tapered at its exterior edges and can have rounded corners. The shape of trailing end 104 itself may be generally quadrilateral, circular, or any other shape useful for the intended purpose.

Trailing end 104 includes bone screw receiving holes 126 for receiving bone screws 128 for securing implant 100 to the adjacent vertebral bodies. Bone screw receiving holes 126 include a gap 130 in the perimeter of bone screw receiving holes 126 for permitting at least a portion of bone screw 128 to protrude beyond perimeter 132 of trailing end 104. Trailing end 104 may be straight, curved, or anatomically contoured. Gap 130 interrupts the perimeter of bone screw receiving holes 126, so that bone screw receiving holes 126 have an incomplete perimeter or C-shape. At least one of the bone screw receiving holes 126 is adapted to cooperatively engage the trailing end of bone screw 128 to allow at least a portion of the perimeter of the trailing end of at least one of the bone screws to protrude beyond at least one of the opposed upper and lower implant surfaces.

As used herein, the trailing end of a bone screw includes not less than that portion of the bone screw at the end opposite the leading end of the screw adapted to cooperatively engage the implant to prevent its passage therethrough. The trailing end may include the head and/or shaft proximate to the head, for example, shaft 134 and head 138 as shown in FIG. 1. The bone screw heads are preferably but not necessarily flush or slightly below the exterior surface of the trailing end of the implant when fully installed so as not to protrude therefrom into anatomical structures that may be present proximate the exterior surface of the trailing end of the implant.

The trailing end of the implant may be configured to receive bone screws such that they are constrained within the bone screw receiving holes (i.e., fixing the trajectory of each bone screw), or left unconstrained within the bone screw receiving holes for allowing variable screw angles. Preferably, for a constrained configuration an interference fit is formed between the wall of the bone screw receiving hole and the screw to prevent the screws from moving within the bone screw receiving hole. Constrained screws may also be self-locking with cooperative mating threads between the screw head and the bone screw receiving hole.

If it is desired that the bone screws are unconstrained then the bone screws may have a rounded head portion and/or a reduced neck diameter to permit movement of the bone screws so as to allow the angle between the implant and the bone screw to be variable.

Bone screws need not be locked to the implant, but simply may have, for example, a shoulder for stopping the progress of a bone screw through the implant beyond a certain point along the bone screw length. It is appreciated that all the bone screws described herein may be self-tapping. Bone screw receiving holes 126 preferably contain a recessed portion 136 to accommodate screw head 138 so that screw head 138 does not substantially protrude away from the trailing end. Gap 130 is sized such that it is less than half the diameter of screw 128. By allowing screws 128 to protrude over edges 140, 142 of trailing end 104, upper and lower screws may be placed such that the maximum height H of trailing end 104 is less than the sum of the maximum diameter of two bone screws adapted to be inserted in bone screw receiving holes 126.

Bone screw receiving holes 126 may be adapted to capture screws 128, thereby constraining the screws within trailing end 104. Alternatively, trailing end 104 can further include at least one locking mechanism 144 for locking the bone screws to implant 100. Although bone screw locks are preferred, the invention is not so limited.

In the various embodiments of the present invention, locking mechanisms 144 and trailing end 104 may be configured to either rigidly capture bone screws 128 so that their positions are fixed, or alternatively allow for the screw angles to be variable in an unconstrained state in which case the screw angles may remain variable when locked.

Locking mechanism 144 can be in the form of a screw or a rivet having a head for contacting and securing the bone screws to implant 100. Locking mechanism 144 may be capable of rotational movement relative to trailing end 104. Locking mechanism 144 includes a tool-engaging portion 146 for moving locking mechanism 144 from an unlocked to a locked position.

Figure 4:
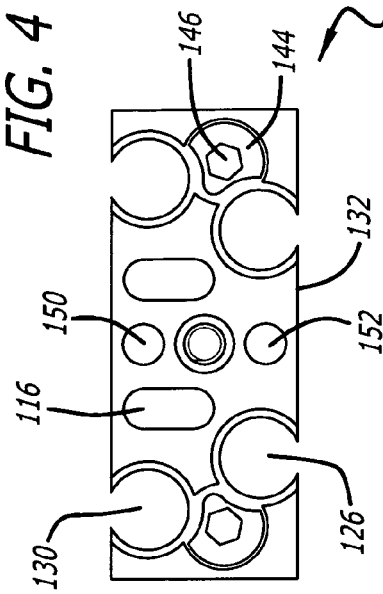
FIG. 4 is a trailing end elevation view of the spinal implant of FIG. 1.
Figure 3:
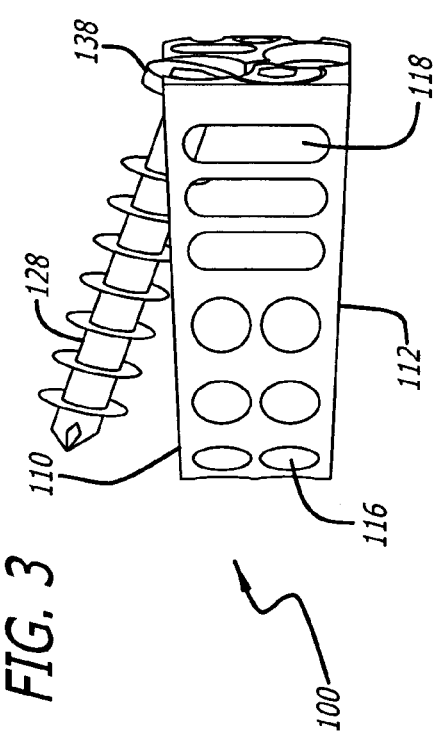
FIG. 3 is a side elevation view of the spinal implant of FIG. 1.

As best shown in FIGS. 1 and 4, locking mechanism 144 further includes removed portions 148 permitting the installation of bone screws into bone screw receiving holes 126 while locking mechanism 144 is in the unlocked position. In a preferred embodiment, locking mechanisms 144 can turn 180 degrees to be fully tightened. Locking mechanisms 144 can turn in the same direction or counter to one another. The bottom of the head of locking mechanism 144 can be of various shapes and, for example, can be ramped or concave. Further, as taught in applicant's application Ser. No. 09/565, 392 titled "Spinal Implant with Vertebral Endplate Engaging Anchor", the present invention may be adapted to receive self-locking screws.

Locks 144 can work either to constrain screws 128 by fixing their positions, or in the alternative by preventing screws 128 from backing out without fixing the screws position so that the screws can allow for settling of the disc space (dynamization).

It is appreciated that the present invention includes the use of other screw locking mechanisms and devices such as would be used in other plate/screw or implant/screw devices and as would be known to one of ordinary skill in the art.

Figure 9:
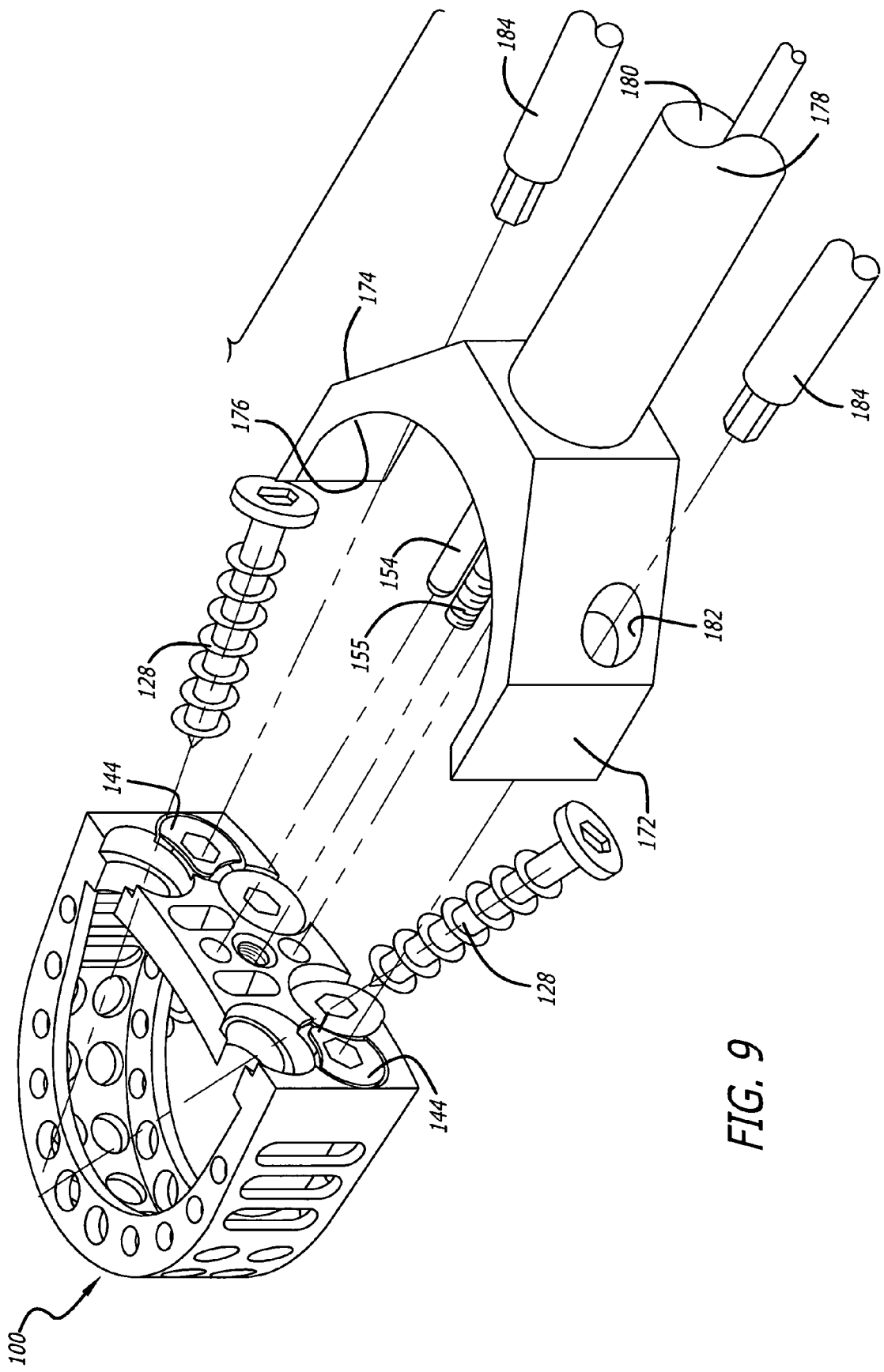
FIG. 9 is an exploded view of the spinal implant of FIG. 8 and a driver holder instrument and locking tool for installing and locking the implant.

As shown in FIG. 9, trailing end 104 further includes alignment holes 150, 152 and threaded engagement hole 153 for engaging alignment pegs 154 and threaded driver 155, respectively from a driver instrument described below. Any other means of engaging the implant to assist in its insertion as would be known in the art is within the scope of the present invention.

A preferred origin and trajectory of bone screw receiving hole 126 is such that a surgeon can (but does not necessarily have to be able to) insert bone screws 128 through holes 126 to an optimal or desired depth without those bone screws crossing a plane bisecting the height of the adjacent vertebral body. An alternative embodiment may include top and bottom screws that are placed asymmetrically so as to be offset from one another so that the screws from such implants inserted into adjacent disc spaces pass each other in an intermediate vertebral body without hitting one another. For example, an implant may have two bone screws in the trailing end toward the outer sides and projecting through the upper surface and one bone screw in the middle of the trailing end projecting through the lower surface.

As shown in FIG. 5, implant 100 is inserted into an implantation space formed across the disc space into the adjacent vertebral bodies. Implant 100 is installed with leading end 102 inserted first into the disc space.

As shown in FIG. 6, bone screw receiving holes 126 may be formed into the adjacent vertebral bodies with a drill 156 and a drill guide 158, an awl, or other device. Drill 156 has a bone removing end 160 and a shaft 162. Drill guide 158 has a leading end 164 adapted for insertion into one of bone screw receiving holes 126 of trailing end 104. Leading end 164 has a smaller dimension 166, a larger dimension 168, and a shoulder 170 corresponding to the reduced dimension portions of bone screw receiving holes 126 that are configured to receive the head portion of bone screws 128. Drill guide 158 has an inner bore (not shown) that in one preferred embodiment is aligned with the central longitudinal axis of the bone screw receiving holes 126 when leading end 164 is properly seated therein. If it is desired to vary the angle of drill guide 158 to bone screw receiving holes 126, the tip of drill guide 158 may be rounded. In the alternative, the drill guide may screw into the bone screw receiving hole, or may attach to the implant by any other technique known in the art. Further, the openings into the bone may be formed with a spike or other device, or the screws may be inserted without first forming bores into the bone.

When drill guide 158 is seated within bone screw receiving hole 126, drill 156 passes through the inner bore to form a bone screw receiving opening into the bone of the adjacent vertebral bodies corresponding in alignment to bone screw receiving holes 126. In the preferred embodiment, bone screw receiving openings 126 are formed in the bone located at or proximate the junction of the two cortices of the vertebral bodies.

In the spinal implant of the present invention, the bone screws can be oriented in an angular relationship to each other so as to be divergent along the vertical plane of the implant when installed into the adjacent vertebral bodies. The preferred angular divergence from the implant surface is preferably 25°-40°, but any angle useful for the intended purpose is within the scope of the present invention. In a preferred embodiment, screws 128 are angled such that they do not extend beyond half the height of the adjacent vertebral body.

This ensures that screws of one implant will not contact the screws of an implant inserted in a neighboring disc space.

In the implant of the present invention, if lag screws are utilized or if there is a lagging implant to screw relationship, then the adjacent vertebral bodies are pulled toward implant 100 as bone screws 128 are installed into the vertebral bone to create a compressive load on the implant. Further, the angling of bone screws 128, keeps the anterior portion of the adjacent vertebral bodies together during extension movement of the spine such as would occur when a patient leans backwards. Among the many advantages of the present invention, the anterior portions of the vertebral bodies adjacent implant 100 do not move apart as they are held in place by bone screws 128 inserted through trailing end 104, the back of the implant is not driven into the vertebral bodies with spinal extension, and the compressive load is safely distributed over the entire length of the interbody portion of the implant.

Figure 7:
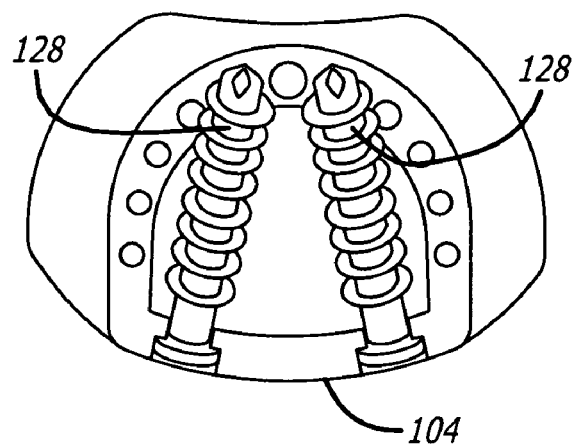
FIG. 7 is a top plan view of the spinal implant of FIGS. 1-4 in the inserted position with bone screws installed and one of the adjacent vertebral bodies shown.

FIG. 7 shows a top plan view of implant 100 installed within the disc space between two adjacent vertebral bodies and bone screws 128 installed in trailing end 104. In a preferred embodiment, bone screws 128 are toed-in toward each other. It is appreciated, however, that bone screws 128 need not be toed-in but may be parallel, diverging, or have any other desired orientation to one another. It is further appreciated that only a single screw or three or more screws can be used to secure the implant to each of the adjacent vertebral bodies instead of the two screws shown in FIG. 7.

Figure 8:
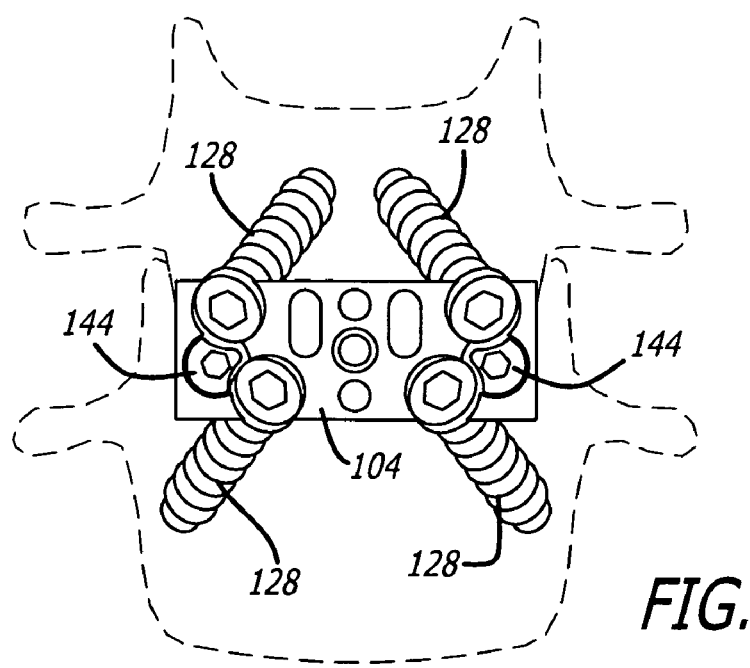
FIG. 8 is a trailing end elevation view of the spinal implant of FIGS. 1-4 installed between two adjacent vertebral bodies shown in hidden line with the locking mechanisms in the unlocked position.

FIG. 8 is a trailing end elevation view of spinal implant 100 installed between two adjacent vertebral bodies with locking mechanisms 144 shown in the unlocked position and bone screws 128 in place. Upper bone screws 128 are converging while lower bone screws 128 are diverging. If two such implants are placed into consecutive disc spaces, converging upper bone screws 128 of one implant and diverging lower bone screws 128 of the other implant would not interfere with each other because of the difference in angulation of the respective bone screws.

As shown in FIG. 9, implant 100 can be installed with driver instrumentation 172 for both holding the implant so as to be useful for insertion and for preventing torquing of the implant when the locks are secured in their locked position. Driver instrumentation 172 has a blocker portion 174 for cooperatively engaging trailing end 104 of implant 100. Blocker 174 has a leading arcuate surface 176 that may be configured to conform at least in part to the contour of trailing end 104. Driver instrumentation 172 has a shaft 178 extending from blocker 174 with of an inner bore 180 along the longitudinal axis of shaft 178. Extending from blocker 174 are a pair of alignment pegs 154 and threaded driver shaft 155 for cooperatively engaging alignment holes 150, 152 and threaded hole 153, respectively, in trailing end 104. Blocker 174 has openings 182 that are coaxially aligned with locking mechanisms 144, respectively. Openings 182 are configured to receive a locking tool 184 therethrough for accessing and operating locking mechanisms 144. Instrumentation 172 allows the surgeon to tighten locking mechanisms 144 against the blocker 174 instead of torquing the spine of the patient.

Driver instrument 172 and blocker 174 are shown as an example of insertion instrumentation with the understanding that any inserter or a blocker or combined inserter and blocker known to one of ordinary skill in the art and useful for the intended purpose is within the scope of the present invention.

Figure 10:
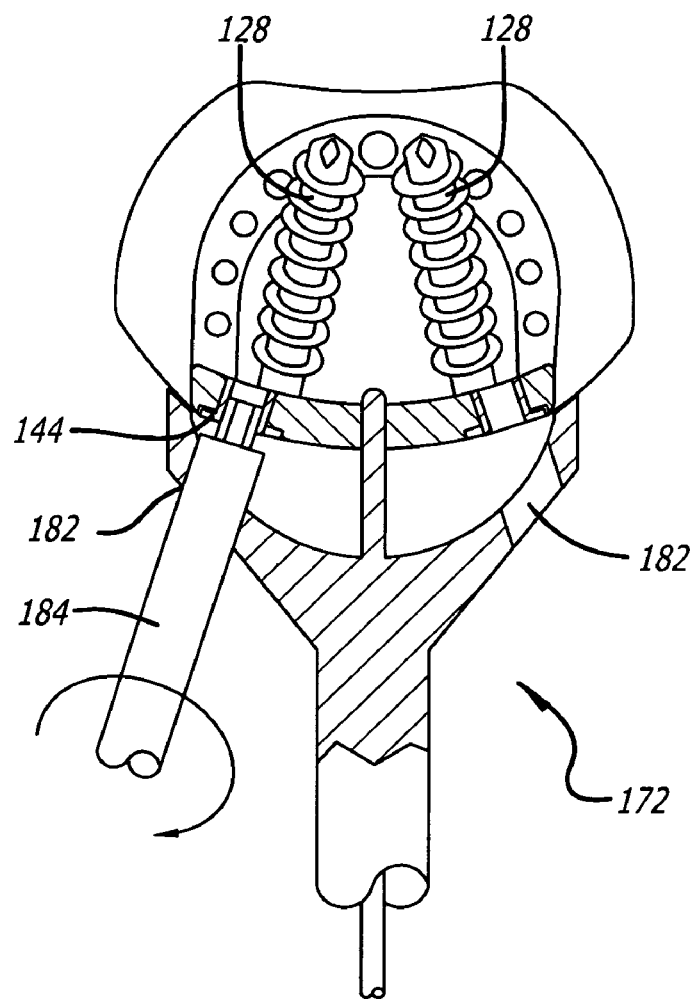
FIG. 10 is a top plan view in partial cross-section of the spinal implant of FIG. 8 and bone screws installed between two adjacent vertebral bodies with the driver holder instrument and locking tool locking one of the locking mechanisms of the implant in the inserted position with one of the adjacent vertebral bodies shown.

FIG. 10 shows a top plan view in partial cross-section of spinal implant 100 installed between two adjacent vertebral bodies and coupled to the driver instrumentation 172 with tool 184 (such as a screw driver) shown locking the locking mechanism 144 (a rivet) to secure bone screws 128 to trailing end 104. It is appreciated that locking mechanism 144 could be a rivet, screw, or the like.

Figure 11:
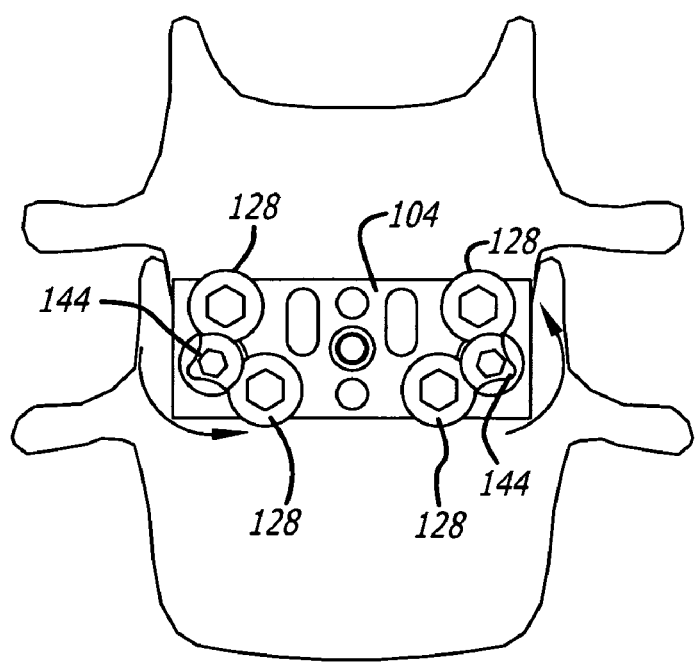
FIG. 11 is a trailing end elevation view of the spinal implant of FIG. 8 with the locking mechanisms shown locking all four bone screws to the implant.

FIG. 11 is a trailing end elevation view of spinal implant 100 installed between two adjacent vertebral bodies with locking mechanisms 144 shown in the locked position in the direction of the arrows to lock bone screws 128 to trailing end 104. It should be understood that either clockwise or counter-clockwise rotational direction can be used for locking screws 128.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

I claim:

1. An orthopedic implant for use in a human body, said implant comprising:
    a distal portion adapted to be placed toward at least one bone of the human body and a proximal portion opposite said distal portion, said proximal portion having a perimeter with a first side and an opposite second side;
    at least a first bone screw receiving hole passing through said proximal portion, said first bone screw receiving hole interrupting at least a portion of said first side of said perimeter to form a first gap in said perimeter, said second side of said perimeter opposite said first gap being uninterrupted by said first bone screw receiving hole; and
    at least a second bone screw receiving hole passing through said proximal portion, said second bone screw receiving hole interrupting at least a portion of said second side of said perimeter to form a second gap in said perimeter, said first side of said perimeter opposite said second gap being uninterrupted by said second bone screw receiving hole.

2. The implant of claim 1, wherein at least one of said bone screw receiving holes is C-shaped in cross section.

3. The implant of claim 1, further comprising a bone screw adapted for insertion through said first bone screw receiving hole, said bone screw having a head and a shaft proximate said head, said shaft having a maximum diameter, said first gap having a maximum dimension less than the maximum diameter of said shaft of said bone screw.

4. The implant of claim 1, wherein said proximal portion of said implant is relieved to allow for a head of a bone screw inserted into one of said bone screw receiving holes to be at least partially recessed.

5. The implant of claim 1, wherein at least two of said bone screw receiving holes are at different distances from a mid-longitudinal axis of said implant.

6. The implant of claim 1, wherein at least one of said first and second bone screw receiving holes is adapted to orient bone screws to be received therein at an angle to a horizontal mid-longitudinal plane of said implant passing through said distal and proximal portions of said implant.

7. The implant of claim 1, further comprising at least one lock for retaining a bone screw to said implant.

8. An orthopedic implant for use in a human body, said implant comprising:
    a distal portion adapted to be placed toward at least one bone of the human body and a proximal portion opposite said distal portion, said proximal portion having first side and an opposite second side;
    at least a first bone screw receiving hole passing through said proximal portion, said first bone screw receiving hole having an incomplete perimeter being interrupted only at said first side of said proximal portion for partially circumferentially surrounding a trailing end of a bone screw; and at least a second bone screw receiving hole passing through said proximal portion, said second bone screw receiving hole having an incomplete perimeter being interrupted only at said second side of said proximal portion for partially circumferentially surrounding a trailing end of another bone screw.

9. The implant of claim 8, wherein at least one of said bone screw receiving holes is C-shaped in cross section.

10. The implant of claim 8, wherein said proximal portion of said implant is relieved to allow for a head of a bone screw inserted into one of said bone screw receiving holes to be at least partially recessed.

11. The implant of claim 8, wherein at least two of said bone screw receiving holes are at different distances from a mid-longitudinal axis of said implant.

12. The implant of claim 8, wherein at least one of said first and second bone screw receiving holes is adapted to orient bone screws to be received therein at an angle to a horizontal mid-longitudinal plane of said implant passing through said distal and proximal portions of said implant.

13. The implant of claim 8, further comprising at least one lock for retaining a bone screw to said implant.

14. An orthopedic implant for use in a human body, said implant comprising:
a distal portion adapted to be placed toward at least one bone of the human body and a proximal portion opposite said distal portion, said proximal portion having a perimeter with a first side and an opposite second side;
at least first and second bone screws each having a leading end for placement in the bone and a trailing end opposite said leading end adapted to contact said implant;
at least a first bone screw receiving hole passing through said proximal portion, said first bone screw receiving hole passing through said first side of said perimeter and having an incomplete perimeter to form a first single gap; and
at least a second bone screw receiving hole passing through said proximal portion, said second bone screw receiving hole passing through said second side of said perimeter and having an incomplete perimeter to form a second single gap.

15. The implant of claim 14, wherein at least one of said bone screw receiving holes is C-shaped in cross section.

16. The implant of claim 14, further comprising a bone screw adapted for insertion through said first bone screw receiving hole, said bone screw having a head and a shaft proximate said head, said shaft having a maximum diameter, said first single gap having a maximum dimension less than the maximum diameter of said shaft of said bone screw.

17. The implant of claim 14, wherein said proximal portion of said implant is relieved to allow for a head of a bone screw inserted into one of said bone screw receiving holes to be at least partially recessed.

18. The implant of claim 14, wherein at least two of said bone screw receiving holes are at different distances from a mid-longitudinal axis of said implant.

19. The implant of claim 14, wherein at least one of said first and second bone screw receiving holes is adapted to orient bone screws to be received therein at an angle to a horizontal mid-longitudinal plane of said implant passing through said distal and proximal portions of said implant.

20. The implant of claim 14, further comprising at least one lock for retaining a bone screw to said implant.

\* \* \* \* \*